United States Patent [19]

Wieringa

[11] Patent Number: 5,106,839

[45] Date of Patent: Apr. 21, 1992

[54] DIBENZODIOXAZECINE AND DIBENZODIOXAAZACYCLOUNDECINE DERIVATIVES

[75] Inventor: Johannes H. Wieringa, BL Heesch, Netherlands

[73] Assignee: Akzo N.V., BM Arnhem, Netherlands

[21] Appl. No.: 601,547

[22] Filed: Oct. 19, 1990

[30] Foreign Application Priority Data

Oct. 20, 1989 [EP] European Pat. Off. ........ 89202653.5

[51] Int. Cl.$^5$ ..................... A61K 31/55; C07D 273/01
[52] U.S. Cl. ..................................... 514/183; 340/468
[58] Field of Search .......................... 540/468; 314/183

[56] References Cited

U.S. PATENT DOCUMENTS 4,374,133  2/1983  Wieringa .............................. 314/183

FOREIGN PATENT DOCUMENTS 2625503  7/1991  France ................................. 540/468

OTHER PUBLICATIONS

Chemical Abstracts vol. 109, No. 21, Nov. 21, 1988, p. 18, Abstract No. 18305n.

Primary Examiner—Robert T. Bond
Attorney, Agent, or Firm—William M. Blackstone

[57] ABSTRACT

Dibenzodioxazecine and dibenzodioxaazacycloundecine derivatives having the general formula I:

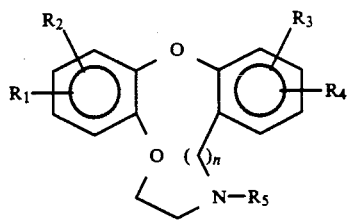

or a pharmaceutically acceptable salt or nitrogen oxide thereof, in which $R_1$, $R_2$, $R_3$ and $R_4$ each represent independently hydrogen, hydroxy, halogen, cyano, alkyl, alkoxy or $CF_3$;

$R_5$ represents hydrogen, alkyl, alkenyl, aralkyl, hydroxyalkyl or acyloxyalkyl; and n represents the number 1 or 2.

The compounds in accordance with the invention are valuable C.N.S. (central nervous systems) active compounds, and in particular possess strong anti-psychotic properties with low propensity to induce extra-pyramidal side effects.

6 Claims, No Drawings

DIBENZODIOXAZECINE AND DIBENZODIOXAAZACYCLOUNDECINE DERIVATIVES

The invention relates to dibenzodioxazecine and dibenzodioxaazacycloundecine derivatives, to processes for their preparation and to pharmaceutical preparations containing the same.

In particular the invention relates to compounds having the general formula I:

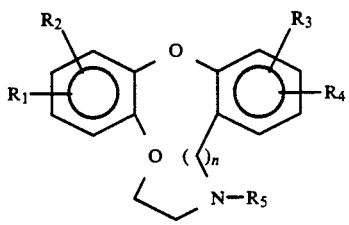

or a pharmaceutically acceptable salt or nitrogen oxide thereof, in which $R_1$, $R_2$, $R_3$ and $R_4$ each represent independently hydrogen, hydroxy, halogen, cyano, alkyl, alkoxy or $CF_3$; $R_5$ represents hydrogen, alkyl, alkenyl, aralkyl, hydroxyalkyl or acyloxyalkyl; and n represents the number 1 or 2.

The compounds in accordance with the invention are valuable C.N.S. (central nervous systems) active compounds, and in particular possess strong anti-psychotic properties with low propensity to induce extra-pyramidal side effects.

The term alkyl group in the definition of $R_1$-$R_5$ means an alkyl group with 1-6 carbon atoms, such as methyl, ethyl, isopropyl, pentyl and hexyl. Alkyl groups with 1-4 carbon atoms are preferred.

The term alkenyl group in the definition of $R_5$ means an alkenyl group with 2-6 carbon atoms, such as allyl and 2-butenyl. Alkenyl groups with 3 or 4 carbon atoms are preferred.

The term aralkyl group means an alkyl group as defined above, substituted with an aromatic group such as phenyl or naphthyl. The said aromatic group can be substituted with one or more alkyl, halogen, hydroxy or alkoxy groups. Preferably the aralkyl group has 7-12 carbon atoms, such as phenylmethyl, phenylethyl, m,p-dihydroxyphenylethyl, m,p-dimethoxyphenylethyl and phenylpropyl.

The alkyl moiety which is present in the alkoxy group has the same meaning as previously defined for alkyl in the definition of $R_1$-$R_5$.

The term hydroxyalkyl group in the definition of $R_5$ means an alkyl group as defined above, substituted with a hydroxy group.

The acyloxy moiety of the acyloxyalkyl group in the definition of $R_5$ is derived from a carboxylic acid with 1-18 carbon atoms, especially from an aliphatic or phenylaliphatic carboxylic acid, such as acetic acid, propionic acid, butyric acid, valeric acid, phenylacetic acid and phenylpropionic acid. Acyloxy groups with 8-18 carbon atoms are preferred. Examples are the octanoyloxy, decanoyloxy, lauroyloxy, myristoyloxy, palmitoyloxy, stearoyloxy and cinnamoyloxy groups. The term halogen means fluorine, bromine, iodine, or, preferably, chlorine.

Preferred compounds according to the invention are compounds of formula I, wherein $R_5$ is methyl, $R_1$ is hydrogen or a 3-chloro group and $R_2$-$R_4$ are hydrogen. More preferred are the compounds in which additionally n has the value 2.

The compounds I are prepared in a manner commonly used for analogous compounds. A suitable method consists of the ring closure of a compound having the formula II,

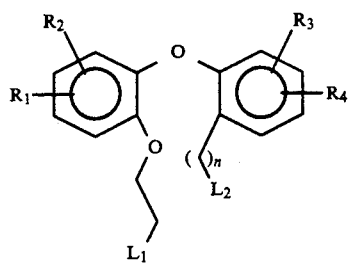

in which $R_1$-$R_4$ and n have the previously given meanings and $L_1$ and $L_2$ represent either both leaving groups or both oxo groups, or one represents a leaving group and the other the group —$NHR_5$, wherein $R_5$ has the previously given meaning. When both $L_1$ and $L_2$ represent a leaving group, such as halogen, of which bromine and particularly chlorine are preferred, or a sulphonyloxy group, ring closure resulting in a compound of formula I takes place by condensation with ammonia or with an amine $H_2NR_5$, wherein $R_5$ has the previously given meaning. $R_5$ in the amine $H_2NR_5$ may also be a suitable protective group, which is cleaved after ring closure to give the group $R_5$ is hydrogen, which may optionally be replaced by another group $R_5$ according to the definition given previously. When both groups $L_1$ and $L_2$ represent oxy groups, the desired product is obtained by reaction with the said amine $H_2NR_5$ in the presence of, or followed by a reaction with, a reducing agent such as lithium aluminum hydride, diisobutylaluminum hydride or sodium borohydride.

Another method consists of the reduction of a compound having the general formula III

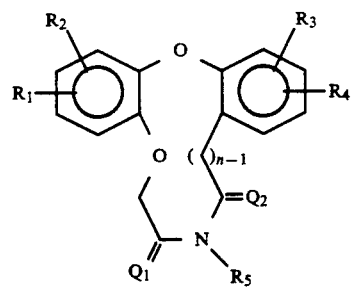

where $R_1$-$R_5$ and n have the previously given meanings, and each of $Q_1$ and $Q_2$ is two hydrogens (2H) or oxygen (O), with the proviso that at least one of the groups $Q_1$ and $Q_2$ represents oxygen.

The reduction takes place in a manner conventionally employed for the reduction of amides and imides, for example with the aid of a complex metal hydride such as lithium aluminum hydride, or with diborane or with boronhydride in dimethylsulphide and tetrahydrofuran.

The compounds of formula II used as starting products are prepared in a manner commonly used for the preparation of such compounds. In the flow sheet a number of synthetic routes to these products has been depicted. It is possible to convert a compound of the invention into another compound of the invention after having carried out one of the aforesaid methods of preparation. Thus, for example, compounds of formula I with $R_5=H$ can be alkylated in the usual manner, for instance by reaction with an alkyl, alkenyl, or aralkyl halide, or by acylating the relevant nitrogen atom and then subsequent reduction of the N-acyl compound thus formed.

The introduction of a methyl group is preferably performed through an Eschweiler-Clarke reaction or through a reaction with formaldehyde and sodium cyanoborohydride in a suitable solvent like acetonitrile.

Another usual method consists of converting the amine I, which is substituted at the nitrogen atom ($R_5$=aralkyl, alkenyl, or alkyl) into the corresponding unsubstituted amine I ($R_5 H$) by means of a de(ar)alk(en-)ylation. Thus an N-benzyl group can be converted in a simple manner by catalytic hydrogenation, or by reaction with an ester of chloroformic acid, or with cyanogen bromide, followed by hydrolysis of the resultant carbamate, into the corresponding NH group. In the case of a carbamate the compound may also be converted into a compound of formula I with $R_5$ methyl by conventional reduction methods.

A conventional hydrolysis of an aromatic alkoxy substituent, and preferably of a methoxy substituent, into the corresponding hydroxy group, for instance by means of an acid such as boron tribromide or hydrobromic acid, may be carried out to obtain compounds of formula I, in which at least one of the groups $R_1$-$R_4$ is hydroxy. An aromatic halogen substituent may be converted into a nitrile by usual methods, for instance by a Rosenmund-von Braun reaction using cuprous cyanide.

The novel compounds of formula I may be isolated from the reaction mixture in the form of a pharmaceutically acceptable salt. The pharmaceutically acceptable salts may also be obtained by treating the free base of formula I with an organic or inorganic acid such as HCl, HBr, HI, $H_2SO_4$, $H_3PO_4$, acetic acid, propionic acid, glycolic acid, maleic acid, malonic acid, fumaric acid, succinic acid, tartaric acid, citric acid, benzoic acid, or ascorbic acid.

The nitrogen oxides I are obtained by oxidation of the nitrogen atom by means of peracids, hydrogen peroxide, or oxidizing metal oxides, such as $MnO_2$.

The compounds according to the invention can be processed to pharmaceutical preparations for enteral administration, local application or parenteral administration by mixing with suitable auxiliaries. A suitable form for administration is a tablet, pill, powder, capsule, paste, spray, sirup, ointment, suppository, solution, suspension or emulsion.

The compounds are usually administered in a dosage of between 0.01 and 50 mg per kg body weight. For administration to humans, the dosage is usually between 1 and 500 mg per day and preferably between 15 and 250 mg per day.

The following examples serve to illustrate the invention.

EXAMPLE 1

3-chloro-7,8,9,10-tetrahydro-8-methyl-6H-dibenzo[b,j][1,4,7]dioxaazacycloundecine (Z)-2-butenedioate (1:1)

A. 5.2 g of sodium methanolate was added portionwise to a stirred solution of 26.1 g of methyl 2-(4-chloro-2-hydroxyphenoxy)benzeneacetate in 260 ml of methanol. After 1 h of stirring at room temperature the mixture was evaporated to dryness and the residue was dissolved in 260 ml of toluene, to which solution were added 10.1 g of α-chloro-N-methylacetamide, 13 g of potassium carbonate and 2.61 g of active copper powder. The mixture was heated to reflux overnight, cooled down and, after filtration over Hyflo, diluted with 500 ml of toluene. After washings with 2N sodium hydroxide and water, the organic layer was dried over sodium sulphate and evaporated to dryness to obtain 32.5 g (85%) of methyl 2-[4-chloro-2-[[(methylamino)carbonyl]methoxy]phenoxy]benzeneacete.

B. 27.2 g of methyl 2-[4-chloro-2-[[(methylamino)carbonyl]methoxy]phenoxy]benzeneacetate was dissolved in 800 ml of dry tetrahydrofuran and slowly added to a suspension of 8.7 g lithium aluminum hydride in 800 ml of dry tetrahydrofuran. The reaction mixture was stirred overnight at 40° C. and after addition of 35 ml of water stirred for another 1 h. The salts were removed by filtration with suction and the filtrate was evaporated in vacuo, to give 20.1 g (84%) of 2-[4-chloro-2-[2-(methylamino)ethoxy]phenoxy]benzene ethanol.

C. A solution of 15 ml of thionylchloride in 200 ml of toluene was added at room temperature to a solution of 20.1 g of 2-[4-chloro-2-[2-(methylamino)ethoxy]phenoxy]benzeneethanol in 400 ml of dry toluene. After 30 min of stirring the mixture was concentrated, dissolved in water and washed with diethyl ether. The aqueous layer was basified with 2N sodium hydroxide and extracted with diethyl ether. The ethereal layer was dried over sodium sulphate, concentrated in vacuo and purified by silica chromatography using toluene-ethanol (8:2) to obtain 12.9 g (61%) of 2-[5-chloro-2-[(2-chloroethyl)phenoxy]phenoxy]-N-methyl-ethylamine.

D. A solution of 9.9 g of 2-[5-chloro-2-[(2-chloroethyl)phenoxy]phenoxy]-N-methyl-ethylamine dissolved in 500 ml of N-methyl-2-pyrrolidone was slowly added to a mixture of 1 l of N-methyl-2-pyrrolidone and 500 ml of pyridine at 85° C. and stirred overnight at this temperature. Water was added, the mixture was extracted with diethyl ether and the ether layer was washed with water and dried over sodium sulphate. The organic solution was evaporated to dryness and the residue was crystallized from dichloromethane-diethyl ether after addition of 1 eq of maleic acid to obtain 2.3 g (28%) of 3-chloro-7,8,9,10-tetrahydro-8-methyl-6H-dibenzo[b,j][1,4,7]dioxaazacycloundecine (Z)-2-butenedioate (1:1). Mp 145–157° C.

In a similar way was prepared 7,8,9,10-tetrahydro-8-methyl-6H-dibenzo[b,j][1,4,7]dioxaazacycloundecine (Z)2-butenedioate (1:1). Mp 152° C.

EXAMPLE 2

3-chloro-7,8,9,10-tetrahydro-8-phenylmethyl-6H-dibenzo [b,j][1,4,7]dioxaazacycloundecine (Z)-2-butenedioate (1.1)

9.1 ml of benzylamine were added to a solution of 7.26 g of 2-(2-bromoethoxy)-1-[2-(2-bromoethyl)-phenoxy]-4-chlorobenzene in 714 ml of xylene and the mixture was heated to reflux for 24 h. After cooling the precipitate was removed with suction, washed with toluene and the filtrate was evaporated to dryness. The residue was chromatographed over silica with toluene-ethanol (9:1) to yield 4,17 g (64%) of 3-chloro-7,8,9,10-tetrahydro-8-phenylmethyl-6H-dibenzo[b,j][1,4,7]dioxaazacycloundecine. $R_f$0.7 (silica; toluene-ethanol 8:2).

EXAMPLE 3 ethyl 3-chloro-7,8,9,10-tetrahydro-6H-dibenzo[b,j][1,4,7]dioxaazacycloundecine-8-carboxylate 4.47 ml of chloroformic acid ethyl ester were added at room temperature to a solution of 4.17 g of 3-chloro-7,8,9,10-tetrahydro-8-phenylmethyl-6H-dibenzo[b,j][1,4,7]dioxaazacycloundecine in 390 ml of toluene. The mixture was heated to reflux overnight, and after cooling shaken with excess of 1N hydrochloric acid. The toluene layer was separated and the acid aqueous layer extracted with diethyl ether. The combined organic extracts were shaken with 1N hydrochloric acid and water, after which the organic layer was concentrated in vacuo and dried azeotropically to yield 3.78 g (95%) of ethyl 3-chloro-7,8,9,10-tetrahydro-6H-dibenzo[b,j][1,4,7]dioxaazacycloundecine-8-carboxylate. $R_f$ 0.6 (silica; hexane-acetone 8:2).

EXAMPLE 4

3-chloro-7,8,9,10-tetrahydro-8-methyl-6H-dibenzob[b,j][1,4,7]dioxaazacycloundecine (Z)-2-butenedioate (1:1)

A suspension of 3.13 g of aluminum trichloride in 110 ml of diethyl ether was added to a suspension of 1.56 g lithium aluminum hydride in 110 ml of diethyl ether and then cooled to approx. 5° C., after which a solution of 4.27 g of ethyl 3-chloro-7,8,9,10-tetrahydro-6H-dibenzo[b,j][1,4,7]dioxaazacycloundecine-8-carboxylate 92 ml of tetrahydrofuran was slowly added. After 1 h the aluminum complex was decomposed by addition of 21 ml of 1N sodium hydroxide solution. After 30 min stirring the salts were removed with suction and rinsed with dichloromethane. After evaporation of the solvent 3.6 g of crude product was obtained, which was purified by silica chromatography with toluene-ethanol (9:1) to obtain pure 3-chloro-7,8,9,10-tetrahydro-8-methyl-6H-dibenzo[b,j][1,4,7]dioxaazacycloundecine. After conversion into the maleate and recrystallization from ethanol-diethylether 2.6 g (52%) of 3-chloro-7,8,9,10-tetrahydro-8-methyl-6H-dibenzo[b,j][1,4,7]dioxaazacycloundecine (Z)-2-butenedioate (1:1), mp 145°-157° C., was obtained.

EXAMPLE 5

6,7,8,9-tetrahydro-8-methyl-dibenzo[b,i][1,4,7]dioxazecine hydrochloride

A solution of 6.2 g of 2-(2-chloroethoxy)-1-[2-(chloromethyl)phenoxy]benzene in 310 ml ethanol was added at room temperature in 45 min to a solution of 80 ml of methylamine in 1.2 l of abs. ethanol. The mixture was stirred overnight, concentrated and dissolved in 100 ml of dimethyl sulphoxide. 18.6 ml of triethylamine were added and the reaction mixture was heated to 90°-100° C. and stirred overnight. After cooling the mixture was poured into 4.5 l of ice water and extracted with 3×600 ml of dichloromethane. The extract was washed with water, dried over sodium sulphate and concentrated in vacuo. The crude product obtained was purified by silica chromatography with dichloromethane-acetone (9:1), after which the free base was converted into the hydrochloric salt, to obtain 2.12 g (35%) of 6,7,8,9-tetrahydro-8-methyl-dibenzo[b,i][1,4,7]dioxazecine hydrochloride. Mp 223° C.

EXAMPLE 6

In an analogous manner as described in Example 5 was prepared 3-chloro-6,7,8,9-tetrahydro-8-methyl-dibenzo [b,i][1,4,7]dioxazecine hydrochloride. Mp 221° C.

FLOW SHEET

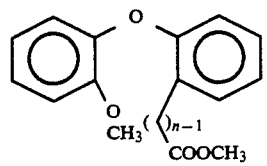

-continued
FLOW SHEET
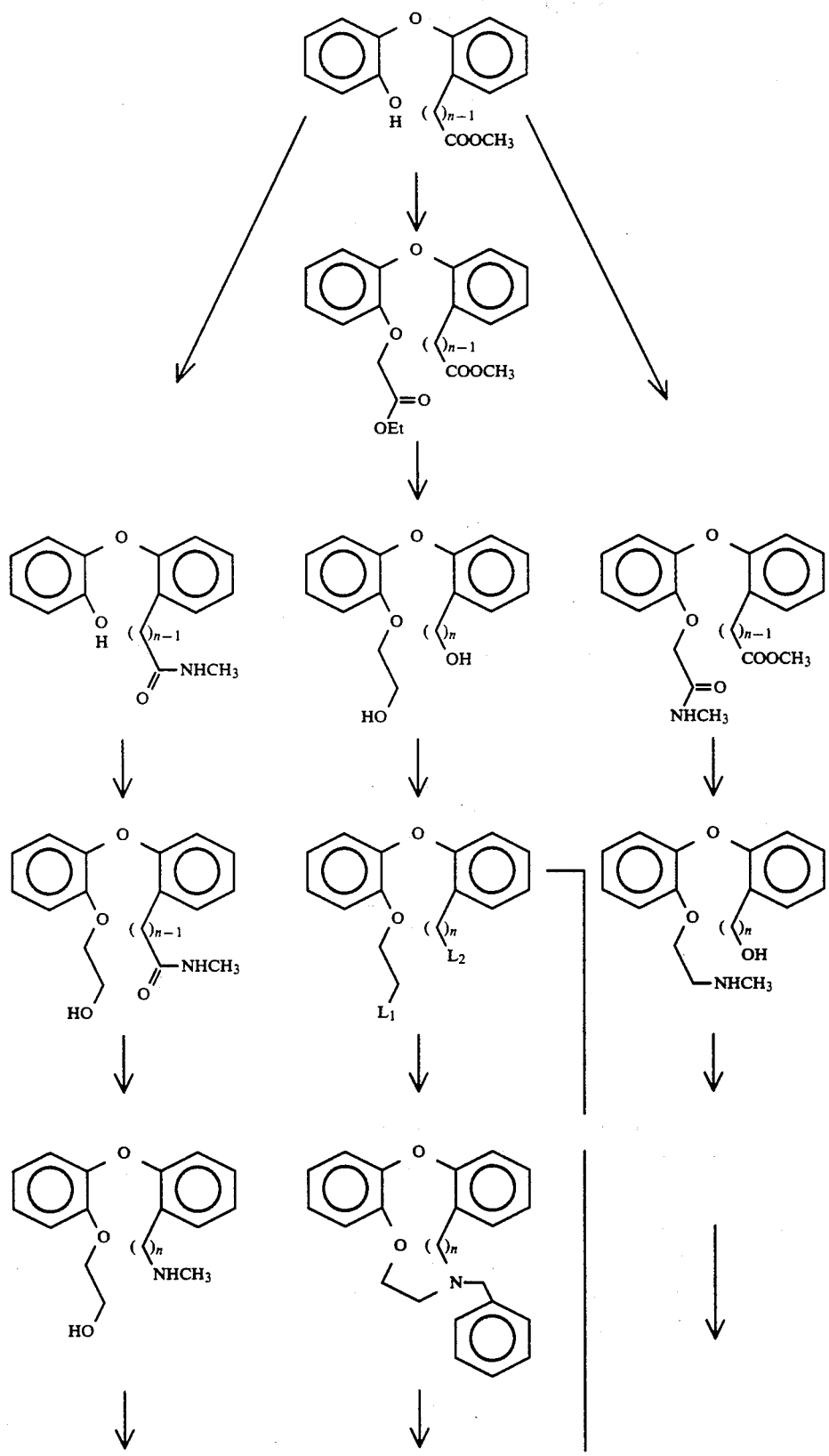

-continued
FLOW SHEET

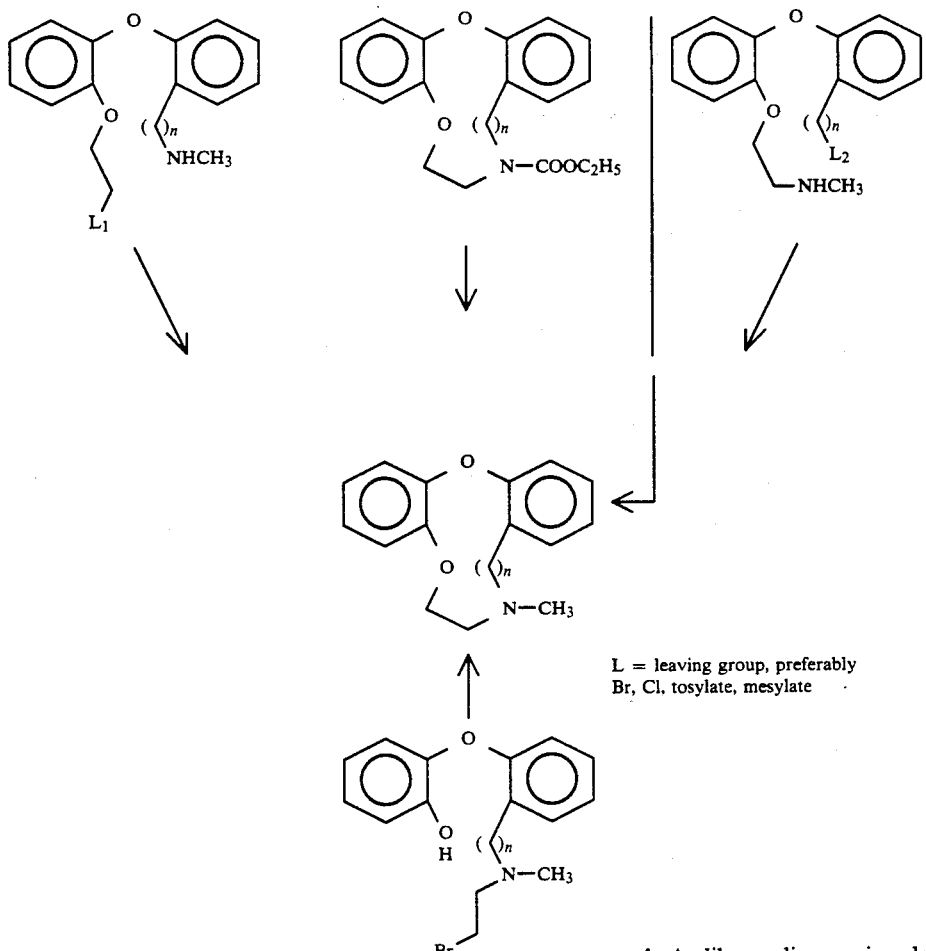

L = leaving group, preferably Br, Cl, tosylate, mesylate

I claim:

1. A dibenzodioxaazacycloundecine derivative having the formula I;

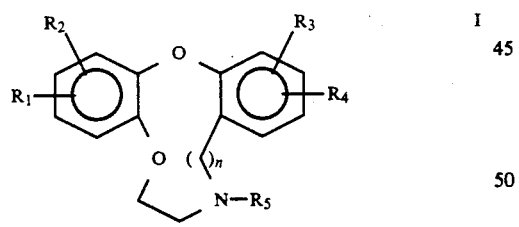

wherein
R$_1$, R$_2$, R$_3$ and R$_4$ each represent independently hydrogen, hydroxy, halogen, cyano, 1-6C alkyl, 1-6C alkoxy or CF$_3$; R$_5$ represents hydrogen, 1-6C alkyl, 2-6C alkenyl, aralkyl that is a 1-6C alkyl substituted with an aromatic group, 1-6C hydroxyalkyl or acyloxyalkyl having an acyloxy moiety with 1-18 carbon atoms; and
n represents the number 2, or a pharmaceutically acceptable salt or nitrogen oxide thereof.

2. Compound according to claim 1, wherein R$_5$ is methyl, R$_1$ is hydrogen or a 3-chloro group and R$_2$-R$_4$ are hydrogen.

3. Pharmaceutical composition comprising therapeutically effective amounts of one or more compounds according to claim 1 to effect anti-psychotic activity in admixture with a pharmaceutically acceptable carrier.

4. A dibenzodioxazecine derivative having the formula I;

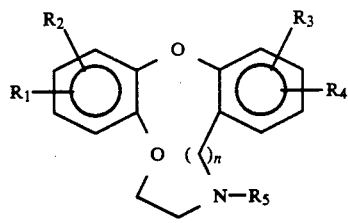

wherein
R$_1$, R$_2$, R$_3$ and R$_4$ each represent independently hydrogen, hydroxy, halogen, cyano, 1-6C alkyl, 1-6C alkoxy or CF$_3$; R$_5$ represents hydrogen, 1-6C alkyl, 2-6C alkenyl, aralkyl that is a 1-6C alkyl substituted with an aromatic group, 1-6C hydroxyalkyl or acyloxyalkyl having an acyloxy moiety with 1-18 carbon atoms; and
n represents the number 1, or a pharmaceutically acceptable salt or nitrogen oxide thereof.

5. Compound according to claim 4, wherein R$_5$ is methyl, R$_1$ is hydrogen or a 3-chloro group and R$_2$-R$_4$ are hydrogen.

6. Pharmaceutical composition comprising therapeutically effective amounts of one or more compounds according to claim 4 to effect anti-psychotic activity in admixture with a pharmaceutically acceptable carrier.

* * * * *